(12) United States Patent
Looper et al.

(10) Patent No.: US 7,122,028 B2
(45) Date of Patent: Oct. 17, 2006

(54) RECONFIGURATION SURGICAL APPARATUS

(75) Inventors: Tony Looper, Mount Prospect, IL (US); David Feng, Arlington Heights, IL (US)

(73) Assignee: Allegiance Corporation, McGaw Park, IL (US)

( * ) Notice: Subject to any disclaimer, the term of this patent is extended or adjusted under 35 U.S.C. 154(b) by 132 days.

(21) Appl. No.: 10/027,343

(22) Filed: Dec. 19, 2001

(65) Prior Publication Data

US 2003/0114839 A1  Jun. 19, 2003

(51) Int. Cl.
*A61B 17/00* (2006.01)

(52) U.S. Cl. .......................... 606/1; 606/205

(58) Field of Classification Search .............. 606/1, 606/170, 174, 205–209; 604/110; 600/104–106, 600/564, 567; D24/135, 143, 146–149; 933/126, 933/141, 144, 146, 147, 157–160; 30/236, 30/260
See application file for complete search history.

(56) References Cited

U.S. PATENT DOCUMENTS

| | | | |
|---|---|---|---|
| 4,569,131 A | 2/1986 | Falk et al. | 30/251 |
| 5,133,735 A | 7/1992 | Slater et al. | 606/205 |
| 5,147,357 A | 9/1992 | Rose et al. | 606/49 |
| 5,304,203 A | 4/1994 | El-Mallawany et al. | 606/207 |
| 5,368,606 A | 11/1994 | Marlow et al. | 606/170 |
| 5,395,375 A * | 3/1995 | Turkel et al. | 606/83 |
| 5,472,439 A * | 12/1995 | Hurd | 606/1 |
| 5,486,185 A * | 1/1996 | Freitas et al. | 606/142 |
| 5,496,333 A * | 3/1996 | Sackier et al. | 606/142 |
| 5,571,137 A | 11/1996 | Marlow et al. | 606/207 |
| 5,593,402 A * | 1/1997 | Patrick | 606/1 |
| 5,618,303 A | 4/1997 | Marlow et al. | 606/205 |
| 5,718,714 A * | 2/1998 | Livneh | 606/205 |
| 5,741,084 A * | 4/1998 | Del Rio et al. | 403/349 |
| 5,766,184 A * | 6/1998 | Matsuno et al. | 606/142 |
| 5,810,879 A * | 9/1998 | de Guillebon | 606/205 |
| 5,817,119 A * | 10/1998 | Klieman et al. | 606/174 |
| 5,934,295 A * | 8/1999 | Gekhter et al. | 132/309 |
| 6,007,561 A * | 12/1999 | Bourque et al. | 606/205 |
| 6,059,719 A * | 5/2000 | Yamamoto et al. | 600/127 |
| 6,228,054 B1 * | 5/2001 | Dysarz | 604/110 |
| 6,273,882 B1 * | 8/2001 | Whittier et al. | 606/1 |

FOREIGN PATENT DOCUMENTS

GB          2227412 A  *  8/1990

* cited by examiner

*Primary Examiner*—Roy D. Gibson
*Assistant Examiner*—Pete Vrettakos
(74) *Attorney, Agent, or Firm*—Donald O. Nickey

(57) ABSTRACT

A reconfigurable surgical apparatus that includes a surgical instrument assembly that is formed with a hollow manipulation shaft. A linearly or rotationally movable prime mover is received within the shaft and is activated by an actuator located at a proximal end. A coupler is formed about a distal end of the shaft to have a capture ledge that is configured to releasably engage an interchangeable surgical tool that is formed with an anchor adapted to releasably mate to the capture ledge. The coupler may optionally incorporate a frangible portion that severs a portion of the coupler when the interchangeable surgical tool is removed from the apparatus to ensure single use operation of the tool.

13 Claims, 3 Drawing Sheets

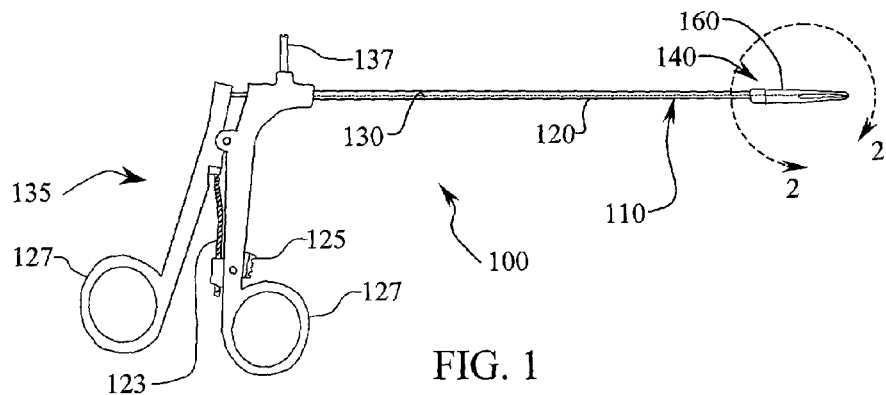
FIG. 1
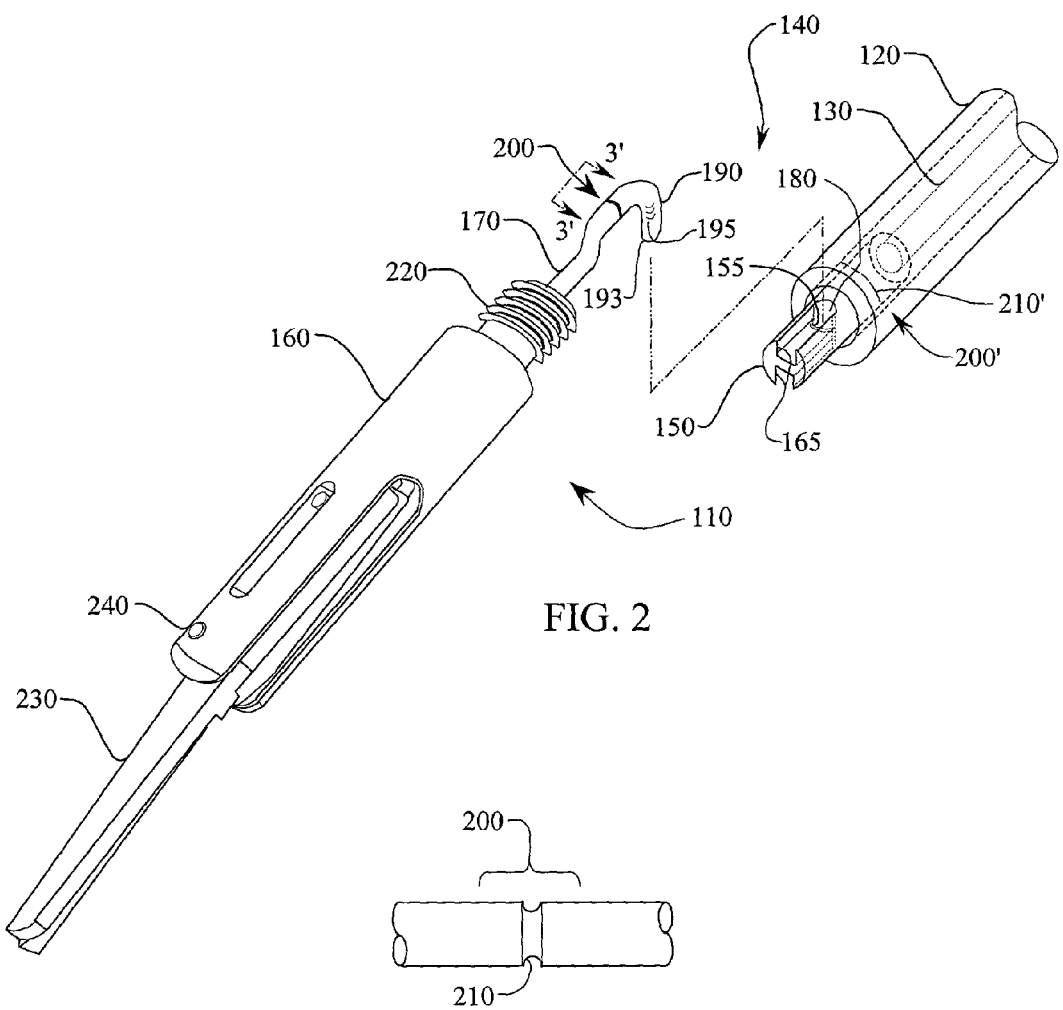
FIG. 2
FIG. 3

RECONFIGURATION SURGICAL APPARATUS

TECHNICAL FIELD

This invention relates to a reconfigurable surgical apparatus and instrument that includes detachable and interchangeable end tools, which incorporate new end tool connectors and couplers.

BACKGROUND OF THE INVENTION

Medical professionals have long-recognized the need for surgical instruments that can utilize a multitude of interchangeable tools. What has been needed but heretofore unavailable are surgical instruments that are compatible for use with detachable and interchangeable tools that incorporate universal connectors that establish interchangeability with a multitude of surgical tools and devices. Such long-felt needs have been particularly prevalent in the field of endoscopic surgical instruments that are used in minimally invasive surgical procedures. These types of procedures are performed through one, two, three, or even four small incisions created in the skin of a patient. In multiple incision procedures, a single endoscopic instrument may be introduced per incision. Each such instrument can typically accommodate, for example, one or two surgical tools that can be manipulated from the exterior of the patient to remotely conduct a specific surgical operation inside the patient. To lessen the trauma to the patient, it is preferable to minimize the number of such incisions and surgical instruments.

The procedures can involve relatively non-complex biopsy procedures as well as very complicated caridiothoracic remedial and interventional operations. In the latter, one or more endoscopic tools are needed to perform the procedure and space inside the body of the patient is at a premium. Therefore, any tools that are to be introduced into the surgical field must compete for space with other tools including for example, clamps, cutting tools, fluid injection and suction ports, lighting and visual equipment, and similar devices. Accordingly, those with skill in the art can appreciate that there is limited intracorporeal space available for tools and equipment. Therefore, before one tool can be introduced, another tool may have to be removed. Since only a limited number of minimally-invasive-type endoscopic surgical instruments are preferably utilized during any given procedure, there has long been a need for the capability to interchange multiple surgical tools on any single endoscopic instrument.

The removability and interchangeability of the tools and reusability of such surgical instrument can reduce costs and complexity. For example, maintenance costs associated with refurbishment, cleaning, and sharpening tools after each surgical procedure is significant. Removable end tools can facilitate such efforts and can also be adapted for single use applications, which eliminates the need for cleaning and refurbishment. During use, biological tissue and fluids can become lodged in the crevices and interstices of small surgical instruments, which complicates sterilization and refurbishment.

Furthermore, the means for connecting the removable tool to the manipulation shaft of the surgical instrument is important to the usefulness of the surgical instrument. The connection must positively secure the components together during operation, and must maintain the connection throughout the range of motion forces typically encountered during surgical procedures. The connection must allow the smooth and controllable transfer of motion from an actuation shaft to the surgical tool. The connection must also facilitate quick and easy connection and disconnection of the interchangeable tool. The connection must be such that it does not become loose and allow movement between the components after repeated use.

Many attempts have been made to create reconfigurable endoscopic instruments that can employ a variety of surgical tools. One such attempt is limited to a medical instrument that incorporates a handle having scissor grips adapted to actuate a manipulation shaft that may be configured, for example, as a grasper, biopsy collector, dissector, or scissor.

Other attempts aimed at reducing maintenance expenses of surgical tools are exemplified by, among other patents, U.S. Pat. No. 4,569,131 to Falk et al. The Falk et al. instrument is a device that has a handle and jaws that are separable from an instrument shaft so that the individual components may be more easily cleaned and sharpened, or disposed of after each use.

Surgical instruments such as that described in U.S. Pat. No. 5,618,303 to Marlowe et al. have attempted to improve joints between components of the instruments. The Marlowe et al. discloses a device that includes a stub shaft or link means terminating in an enlarged end that is shaped to be received by a clevis. Other types of joints are described in U.S. Pat. No. 5,304,203 to El-Mallawany et al., which teaches a T-shaped coupling joint.

What continues to be needed but missing from the field of interchangeable surgical tools is a secure connection between components of a surgical instrument that will not loosen after several uses, which is also designed for improved ease of manufacture and replaceability. While some of the prior art devices attempted to improve the state of the art of interchangeable surgical tools, none has achieved low cost part that is easy to fabricate and convenient to use. A more desirable interchangeable surgical tool would preferably include a more secure connection, which can be adapted so that different tools can be configured to the surgical instrument. With these capabilities taken into consideration, the instant invention addresses many of the shortcomings of the prior art and offers significant benefits heretofore unavailable.

SUMMARY OF THE INVENTION

In its most general sense, the present invention overcomes the shortcomings and limitations of the prior art in any of a number of generally effective configurations. In one configuration, the reconfigurable surgical apparatus or instrument according to the present invention incorporates, among other elements, a prime mover that is movably positioned within a hollow manipulation shaft. The prime mover is adapted to be activated by an actuator located at a proximal end of the shaft. The shaft also includes a coupler at the distal end which comprises a capture ledge. The surgical apparatus is further configured with an interchangeable surgical tool that is attached to the coupler. The tool also includes an anchor that is adapted to releasably mate to the capture ledge of the coupler.

Thus, there is disclosed a reconfigurable surgical apparatus comprising a surgical instrument assembly formed with a hollow manipulation shaft receiving a prime mover activated by an actuator located at a proximal end of the shaft. The surgical apparatus also includes a coupler formed about a distal end of the shaft with a capture ledge. Further, there is an interchangeable surgical tool which is attachable to the coupler which includes an anchor adapted to releasably mate to the capture ledge.

The coupler is preferably configured to have the capture ledge define a surface or a portion of a surface of at least one lateral aperture or slot, which is sized to releasably receive the anchor. The anchor and the capture ledge are arranged to cooperate during actuation of the prime mover.

In one of many variations of the instant invention, the anchor can be formed as a generally hook shaped tine that is sized and shaped for releasable receipt into the slot and against the capture ledge. The hook shaped tine may also further include an engagement face that is adapted to releasably engage and cooperate with the capture ledge.

Any of the preceding configurations and embodiments may also be adapted with the anchor having a frangible portion. In certain implementations, it may be desired to limit use of the end tool and/or the entire reconfigurable surgical apparatus to a single use. This would ensure the sterility of the apparatus and/or the end tool prior to use.

The frangible portion may be defined by at least one shear notch. In alternative arrangements, the frangible portion can also be formed to be a weakened material having shear strength that is less than that of the surrounding material. This can be accomplished with either integrally extruded or joined dissimilar materials, or by forming the frangible portion to have a smaller diameter, a scored section, or a notched portion. Such scoring or notches may be a portion of or the entire circumference of a section of the anchor.

Thus, there is further disclosed a reconfigurable surgical apparatus comprising a surgical instrument assembly formed with a hollow manipulation shaft receiving a prime mover activated by an actuator located at a proximal end of the shaft. A coupler is formed about a distal end of the shaft having a capture ledge that defines a slot in the coupler. An interchangeable surgical tool adapted to connect to the coupler comprises a frangible portion and an anchor adapted to releasably mate to the capture ledge. The frangible portion is adapted for receipt in the slot after the anchor has been removed from the tool. Also disclosed is a reconfigurable surgical apparatus comprising a surgical instrument assembly formed with a with a hollow manipulation shaft receiving a prime mover activated by an actuator located at a proximal end of the shaft. A coupler is formed about a distal end of the shaft having a capture ledge that defines a lateral slot in the coupler. An interchangeable surgical for attachment to the coupler and formed with an anchor having a shear notch. The anchor may be adapted to releasably mate to the capture ledge and severed from the tool about the notch.

As described in the various figures, the frangible portion preferably causes a distal section of the anchor to sever or shear apart upon disconnection from the coupler. While complete shearing of the distal section is preferable in most configurations, it is not necessary for ensuring that the reconfigurable surgical apparatus is not reused prior to inspection, refurbishment, and replacement of worn or unserviceable components. All that is required in instances where reuse is to be restricted, controlled, or prevented, is that the end tool be prevented from proper coupling to the surgical apparatus. The present invention contemplates many suitable arrangements that are capable of accomplishing such described capabilities. Preventing reuse can be accomplished by incorporating a semi-frangible, distortable, or distendible portion that will deform upon decoupling of the end tool from the distal end of the shaft. In one embodiment, the frangible portion is completely severable and the severed end of the anchor that remains on the tool may be used as a probe that can be inserted into the lateral slot to remove the portion of the severed anchor. The present invention further contemplates that the distal end of the shaft is adapted to incorporate the anchor and the interchangeable tool and is formed with the capture ledge which is adapted to releasably mate to the anchor. This is opposite to the arrangement where the anchor depends from the end tool and the capture ledge and/or the lateral slot is formed in the distal end of the shaft. As in preceding configurations, the lateral slot and the capture ledge are preferably adapted to releasably receive the anchor.

In a further variation of any of the preceding embodiments, the instant invention is also directed to the reconfigurable surgical apparatus that includes the interchangeable surgical tool being configured to connect to the coupler and having a reciprocating capture member adapted to releasably mate to the anchor. The reciprocating capture member preferably receives the anchor described in previous embodiments and variations and operates to actuate the particular end tool as the anchor-capture member moves in response to linear motion inputs from the actuator.

As with preceding configurations, modifications, and alternatives, the capture member of the instant variation may be formed in the end tool to define at least one lateral recess adapted to releasably receive the anchor. One of many modifications of the anchor includes a generally hook shaped tine having an end sized for releasable receipt into the recess of the member. As before, the hook shaped tine may include an engagement face adapted to releasably engage the capture member.

In yet another configuration, the reconfigurable surgical apparatus according to the present invention includes, among other elements, a surgical instrument assembly having the coupler formed about the distal end of the shaft to include a receiver formed with an engagement ledge and shelf. The assembly also incorporates an interchangeable surgical end tool that is attached to the coupler, and which includes an engager that is adapted to releasably mate to the receiver.

The preferred receiver according to the invention includes a generally hook shaped recess that is adapted to releasably mate with the engager. Further, the engager is formed with a generally hook shaped projection that is formed to releasably mate with the receiver. Thus, there is disclosed a reconfigurable surgical tool comprising a surgical instrument assembly formed with a hollow manipulation shaft receiving a prime mover activated by an actuator located at a proximal end of the shaft. A coupler formed about the distal end of the shaft includes a receiver having an engagement ledge and shelf and an interchangeable surgical tool attachable to the coupler contains an engager adapted to releasably mate to the receiver.

A further variation of the engager-receiver configuration can incorporate a frangible portion that is similar in operation to any of the preceding arrangements. More specifically, the frangible portion may be configured to, among other features and capabilities, limit the interchangeable surgical end tool to a single use so as to afford an opportunity for a post-use safety and serviceability inspection and for refurbishment and replacement of components or the entire end tool. Additionally, the frangible portion may incorporate any of the previously described features, elements, and capabilities, and may be defined as one or more shear notches, which notches may be confined to a small region of the exterior circumference of the shaft of the engager, the receiver, or both. Also, the one or more notches may be circumferentially formed so as to establish one or more regions of the engager-receiver coupler that is/are of a generally reduced diameter relative to the non-notched portion thereof.

Thus, there is further disclosed a reconfigurable surgical tool comprising a surgical instrument assembly formed with a hollow manipulation shaft receiving a prime mover activated by an actuator located at a proximal end of the shaft. A coupler formed about the distal end of the shaft is formed with an engager and an interchangeable surgical tool formed with a receiver with an engagement ledge and shelf is adapted to releasably mate to the engager.

Preferably, the frangible portion establishes a region of the engager-receiver coupler that is weakened relative to the surrounding structure. Even more preferably, the comparatively weakened region serves as a fracture zone that severs the engager from the surgical end tool, or from the shaft in alternative arrangements, when the surgical tool is decoupled from the surgical instrument assembly. As with prior embodiments, variations, and modifications, the severed end portion of the engager that remains can be used to remove the portion of the anchor that may remain engaged with the capture ledge and in the lateral slot.

In yet other alternatives to any of the above-described configurations, the engager and receiver may be formed in alternate positions whereby the engager depends from the distal end of the prime mover, and the receiver is incorporated into the surgical tool. Additionally, the receiver, in any of the preceding embodiments, may further define a generally hook shaped recess that can be adapted to releasably receive the engager. The engager may also be formed with a generally hook shaped projection that is sized and configured to be releasably received in the recess to effect the releasable mating to the receiver.

These variations, modifications, alternatives, and alterations of the various preferred embodiments, arrangements, and configurations may be used alone or in combination with one another as will become more readily apparent to those with skill in the art with reference to the following detailed description of the preferred embodiments and the accompanying figures and drawings.

Also, the present invention relates to a means for performing an intracorporeal surgical procedure comprising a means for imparting a range of motion and a means for defining an intracorporeal passageway connected to a passageway connected at a proximal end to the motion-imparting means, the passageway being received with a means for transmitting the imparted range of motion. This intracorporeal surgical procedure also comprises a means for distally coupling the passageway means that defines a means for interchangeably capturing and an interchangeable means for performing a surgical intervention that includes a means for releasably mating the intervention means to the capturing means wherein the interchangeable intervention means is, when mated to the capturing means remotely actuatable by operation of the motion imparting means.

Further, the invention relates to a means for imparting a range of motion and a means for defining an intracorporeal passageway connected to a proximal end to the motion-imparting means, the passageway being received with a means for transmitting the imparted range of motion. This intracorporeal surgical procedure also comprises a means for distally coupling the passageway means that defines a means for anchoring and an interchangeable means for performing a surgical intervention that includes a means for releasably capturing the anchoring means wherein the interchangeable intervention means is, when mated to the anchoring means remotely actuatable by operation of the motion imparting means.

BRIEF DESCRIPTION OF THE DRAWINGS

Without limiting the scope of the present invention as claimed below and referring now to the drawings and figures, wherein like reference numerals and numerals with primes and double primes across the several drawings, figures, and views refer to identical, corresponding, or equivalent elements, features, and parts:

FIG. 1 is an elevation view, in reduced scale, of a reconfigurable surgical apparatus according to the present invention;

FIG. 2 is a detail perspective exploded view, in enlarged scale and rotated, of the reconfigurable surgical apparatus shown in FIG. 1 within detail view line 2—2;

FIG. 3 is a side view, in enlarged scale and rotated, taken along section line 3'—3' of FIG. 2;

DESCRIPTION OF THE PREFERRED EMBODIMENTS

The apparatus of the instant invention provides a significant advance in the state of the art of interchangeable surgical tools. The preferred embodiments of the reconfigurable end surgical tool accomplish this by new and novel arrangements of elements that are configured in unique and novel ways and which demonstrate previously unavailable but preferred and desirable capabilities.

The detailed description set forth below in connection with the drawings is intended merely as a description of the presently preferred embodiments of the invention, and is not intended to represent the only form in which the present invention may be constructed or utilized. The description sets forth the designs, functions, means, and methods of implementing the invention in connection with the illustrated embodiments. It is to be understood, however, that the same or equivalent functions and features may be accomplished by different embodiments that are also intended to be encompassed within the spirit and scope of the invention.

Figure 4:
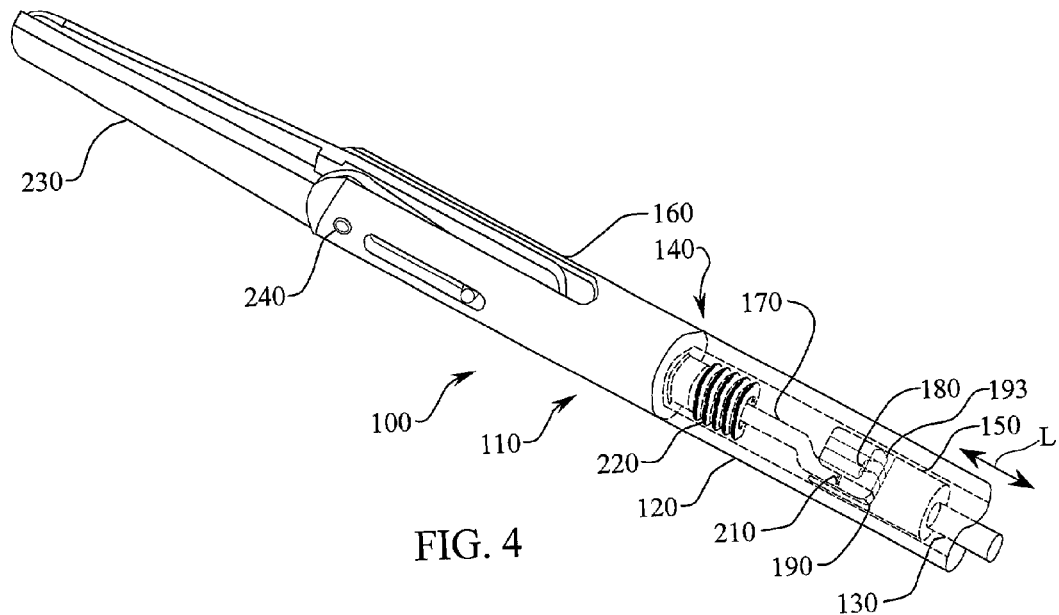
FIG. 4 is a rotated perspective view of the assembled reconfigurable surgical apparatus shown in FIG. 2.

With reference generally now to FIGS. 1 through 6, and more specifically to FIGS. 1, 2, and 4, in one of the many preferable arrangements, the reconfigurable surgical apparatus 100 according to the present invention includes, among other elements, a surgical instrument assembly 110. The assembly 110 also includes a prime mover 130 that can be positioned within a hollow manipulation shaft 120 and which is adapted to impart a range of motion. The prime mover 130 is activated by an actuator 135 located at a proximal end of the shaft 120, which is configured to remotely impart the desired range of motion. Various types of manually, remotely, mechanically, and automated actuators are known to those with skill in the art. As described generally in the various figures and as shown in FIG. 1 for purposes of an exemplar, a manual scissors handle-type actuator 135 can be employed for purposes of the present invention. Although the hollow manipulation shaft 120 is shown with a single lumen, it can be formed with multiple lumens that can be adapted for receipt of various other elements in addition to the prime mover 130. Additionally, the entire reconfigurable surgical apparatus 100 can be sized and configured for receipt within a larger minimally invasive surgical instrument that is introduced intracorporeally and which is adapted to receive the surgical apparatus 100 contemplated herein.

In exemplary configurations, the actuator 135 is adapted to cooperate with a rigging cord 123 that is adjusted with a release latch 125. The cord 123 is preferably linked or directly connected to the prime mover 130 and is adjusted to control the range of motion of the prime mover when the handles 127 of the actuator 135 are operated. In variations of the present invention, the actuator 135 may also incorporate one or more ports 137 that can be adapted to receive additional elements such as fluid lumens and additional prime movers that can be configured to add further functionality and more complex motion to the instrument assembly 110. For example, a directional guide wire (not shown but known to those having skill in the art) can be received through the port 137. Such a guide wire is useful and can facilitate intracorporeal introduction of the surgical instrument assembly 110 during minimally invasive surgical procedures that require insertion of the instrument 110 through cutaneous incisions and ports in the body of a patient. The prime mover 130 is shown in the figures as configured for linear motion, however, the mover 130 can be augmented and or replaced with a similar element (not shown but within the skill in the art) that can be configured for rotational motion. Also, those having ordinary skill in the art can understand that either of such elements, the prime mover 130 or such other elements, can be configured for both linear and rotational motion in certain arrangements of the surgical instrument 110.

With continued reference to the various figures and specifically now also to FIG. 2, the surgical instrument assembly 110 also further incorporates a coupler 140 that is formed about a distal end of the shaft 120. In one of various arrangements, the coupler 140 incorporates a capture member 150 that is formed with a capture ledge 155. The surgical instrument assembly 110 is compatible for use with and includes any of a wide number of end effectors that are selected according to the surgical intervention to be accomplished. For example, such end effectors can include application specific interventional tools, such as scalpels, dissectors, biopsy collectors, drills, tweezers, scissors, catheters, lumens, stents, balloons, as well as active and passive observational probe, visual, and illumination devices, and combinations thereof. For purposes of illustration but not limitation, the instrument 110 of the various figures is shown to include an interchangeable surgical tool 160 in the general form of a scissors. The coupler 140 also includes one or more cooperating elements on the interchangeable surgical tool 160, which are adapted to connect the tool 160 to the coupler or coupling mechanism 140 portion that depends from the distal end of the shaft 120. In this configuration, the coupler 140 incorporates an anchor 170 that is adapted to releasably mate with the capture ledge 155.

In the exemplary arrangement of the instant invention shown in FIG. 2, the coupler 140 portion of the interchangeable surgical tool 160 is preferably formed to define at least one lateral aperture or slot 180 that includes at least one surface that can be the capture ledge 155. The capture ledge 155 and the slot 180 can be formed and arranged to releasably receive and retain the anchor 170. Any of a large number possible anchor configurations may be suitable for purposes of the present invention, and can include, for purposes of illustration but not limitation, the anchor 170 formed as a generally hook shaped tine 190 that has an end 193, which tine 190 and end 193 are preferably sized for releasable receipt into the slot 180. The hook shaped tine 190 may also further include an engagement face 195 that is adapted to releasably engage the capture ledge 155.

Although generally featureless surfaces are shown about the ledge 155, on the engagement face 195, and in the slot 180 in the various figures, the present invention contemplates further modifications to the ledge 155, the face 195, and the slot 180 wherein the respective surfaces can be modified for additional functionality and interoperability. For example without limitation, the engagement face 195 and the ledge 155 may be modified to incorporate cooperating and/or locking features, such as gear teeth and notches that operate to mesh together upon receipt of the anchor 170 in the slot 180. Other alternative configurations may include surface textures adapted to create further enhancements to the interface between the slot 190, the engagement face 195, and the capture ledge 155. One such variation can include a unidirectional tooth and pawl ratchet mechanism wherein ramp or tooth-type structures are formed on the engagement face 195 and one or more pawl-type structures are formed on or about the hook shaped tine 190.

Examples of such locking features that are known in the art include, for example without limitation, wire and cable tie devices such as those disclosed in U.S. Pat. Nos. 4,214,349 and 4,135,749, which are collectively incorporate herein by reference in their entirety. Incorporation of such features into the device according to the present invention can be desirable for applications wherein the interchangeable surgical tool 160 is to be used one time only or where the tool must be inspected and refurbished between uses to ensure safety and operability. With such ratcheting features, the tine 190 of anchor 170 can be snapped, threaded, or inserted into the slot 180 in one direction, but cannot be removed therefrom in the retrograde direction. In this preferred variation, the tine 190 can be removed from the slot 180 only after being severed from the anchor 170 and then by being threading out of the slot 180 in the required direction.

Any of the preceding and later described embodiments of the apparatus 100 may also further optionally incorporate one or more orientation and alignment slots or keyways 165 that may be formed in any of the components and elements of the instant invention and which are operative to facilitate alignment of the capture member 150 and the anchor 170 of the coupler 140. As reflected in FIGS. 2 and 4, two generally longitudinal keyways are formed in the capture member 150 and are adapted to nestingly receive a segment of the installed anchor 170.

Prior to operation and use of the reconfigurable surgical apparatus 100 according to the instant invention, the anchor 170 is engaged with the capture ledge 155 wherein the hook shaped tine 190 is received in the slot 180. Next, the capture member 150 is retracted into the hollow manipulation shaft 120, and the interchangeable surgical tool 160 is secured to the shaft 120 with the connector 220. The connector 220 may take the form of any of a number of connection devices including, for example without limitation, threads, twist and lock type elements that operate with partial relative rotation much like the so-called child-proof medicine bottle caps and automotive gas tank filler port caps, pin and clevis connectors, clamp and post type frictional connectors, chuck and pin type devices that operate in an manner similar to that of drill bits and chucks, key and keyway and cotter couplers, bayonet type connectors similar to those used in camera lens mounts and in some computer related network cabling components, and scarf joint type couplers. In one of many variations, the connector 220 may take the form of a threaded connection, as shown for purposes of illustration in FIGS. 2, and 4 through 6. In this variation, the male connector threads 220 are receivably engaged with cooperating female threads formed within the coupler 140 at the distal end of the manipulation shaft 120.

With continued reference to the various figures and illustrations, and with specific reference now also to FIGS. 2, 3, and 4, those possessed with skill in the art can observe that the reconfigurable surgical apparatus 100 is assembled and nearly ready for use once the connector 220 is engaged and the coupler 140 joins the interchangeable surgical end effector or tool 160 to the surgical instrument assembly 110. After the coupler 140 is secured, the user typically rigs the apparatus 100 for operation by, as noted generally hereinabove by releasing the adjustment cord release latch 125 and adjusting the actuator cord 123 so as to establish the desired range of linear motion, as opposed to rotational motion that may be imparted with a different type of actuator that that depicted in the various figures. For continued purposes of illustration, the described linear motion of the prime mover 130 is shown generally by the arrows of FIG. 4 that are identified by reference letter "L". In this arrangement, the linear motion of the prime mover 130 can, during operation of the actuator 135, be transferred through the capture member 150, to the hook shaped tine 190 of the anchor 170, to in turn actuate the interchangeable surgical tool 160.

With specific reference also now to FIG. 3, a further variation of the reconfigurable surgical apparatus 100 includes a frangible portion 200, which in the various figures is reflected to be in the anchor 170. The frangible portion 200 can be incorporated to limit the interchangeable surgical tool 160 to a single use, which can be required in a number of circumstances. Most commonly, in recognition of the wear and deterioration that can result from normal use of the surgical tool 160, it has been seen to be desirable that the tool 160 be limited to single use applications. This requirement and need is especially pronounced in circumstances where the surgical tool 160 may be constructed of less expensive, recyclable, light-weight, or hybrid materials that are more susceptible to failure after repeated use. Alternatively, such need for elements, such as frangible portion 200, which limit multiple use can arise in procedures that result in extensive wear on the surgical tool 160 that is fabricated from the more durable materials such corrosion resistant and stainless steels and advanced shape memory alloys thereof. Such high-strength and durable materials can experience significant wear even after only a single use. This has been demonstrated in a variety of routine surgical interventions including, for illustration purposes without limitation, procedures performed on bone tissue and that may require the location and removal of foreign bodies such as chipped bone fragments, calcified deposits, and other undesirable objects such as loosened or ajar bone repair screws, and inadvertently misplaced surgical instruments and fragments thereof, most of which may need to be cut into smaller parts prior to removal.

Any of the preceding embodiments, configurations, and variations of the present invention may be modified to incorporate the frangible portion 200, which may be constructed in any of a number of ways, and in any number of locations about the reconfigurable surgical apparatus 100. Preferably, the frangible portion 200 is formed on either the surgical instrument assembly 110 or the interchangeable surgical tool 160, or both, proximate to the coupler 140. More preferably, the frangible portion 200 is formed about either the anchor 170 or the capture member 150.

For purposes of continued illustration, the frangible portion 200 reflected in the various figures, including FIGS. 2 and 3 is shown to be formed as a circumferential region of reduced diameter, or a generally toroidal, parabolic, or counter-sink shaped shear-type notch 210 that is formed about a portion of the anchor 170. A similar frangible portion (not shown) can be implemented wherein the frangible portion 200 may be replaced or augmented with a region that is formed by a material of construction of the anchor 170 in the region of the frangible portion 200 to be weaker than the surrounding material of the anchor 170. This can be accomplished with either a non-circumferential notch, a diametrical or lateral recess formed in the anchor 170, or functional equivalents thereof. In yet additional examples, the frangible portion 200 may also be formed wherein the material of the anchor 170 material is selected to have a material strength that is reduced in the region of the frangible portion 200 relative to the other portions of the anchor 170. Another variation may include forming a circumferential score about the anchor 170 in the region of the frangible portion 200. An additional method includes forming at least one non-circumferential shear notch, which may be similar in cross-section to the notch 210, within the frangible portion 200 by removing material from the anchor 170 by machining, or by molding the anchor 170 to have the illlustrated shear notch 210 or some similar feature.

Those with skill in the art can appreciate that the frangible portion 200, or shear notch 210, according to the preferred examples, may be incorporated in any number of locations along the anchor 170, or other components and elements of the apparatus 100. FIGS. 2 and 4 illustrate only one such position, from among many possible locations of the apparatus 100, along the portion of the anchor 170 that is located proximate to the capture ledge 155, when the coupler 140 is in the assembled configuration. Another alternative or additional location of the frangible portion 200, or shear notch 210, is on a segment of the hook shaped tine 190. The tine location facilitates the embodiment previously described in which the hook shaped tine 190 cannot be removed from the slot 180 unless the tine 190 is sheared from the anchor 170. This variation leaves the straight portion of the tine 190 in the slot 180, where it can be forced out of the slot 180 by using the severed end of the anchor 170 that remains on and depends from the tool 160 after severing. In operation of the frangible portion 200 during decoupling of the tool 160 from the instrument assembly 110, the frangible portion 200 of the anchor 170 of the surgical tool 160 is severed after disconnection from the coupler 140. The apparatus 100 may be configured whereby the severing operation occurs immediately upon decoupling the coupler 140 by unthreading the connector 220. Alternatively, the severing operation can be performed manually after the tool 160 is disconnected from the distal end of the shaft 120. As described above, the portion of the anchor 170 that remains on the tool 160 may then be used to remove the portion of the anchor 170 remaining in the capture ledge 155 from the lateral slot 180 by pushing the severed end into the slot to dislodge the severed segment of the tine 190. Referring again to FIG. 2, a further optional variation of the capture member 150 includes a frangible portion 200' that is formed in the capture member 150. The frangible portion 200' may be formed by any of the previously detailed means.

As already described, many various types of interchangeable surgical tools 160 are contemplated for use with the present invention. As reflected in the various figures for purposes of illustration, a tool 160 is shown that is compatible for use with reciprocating linear motion during operation. More specifically, the various figures depict the tool 160 to be an endoscopic scissors tool having blades 230 adapted to move about pivot pin 240 during actuation.

Figure 5:
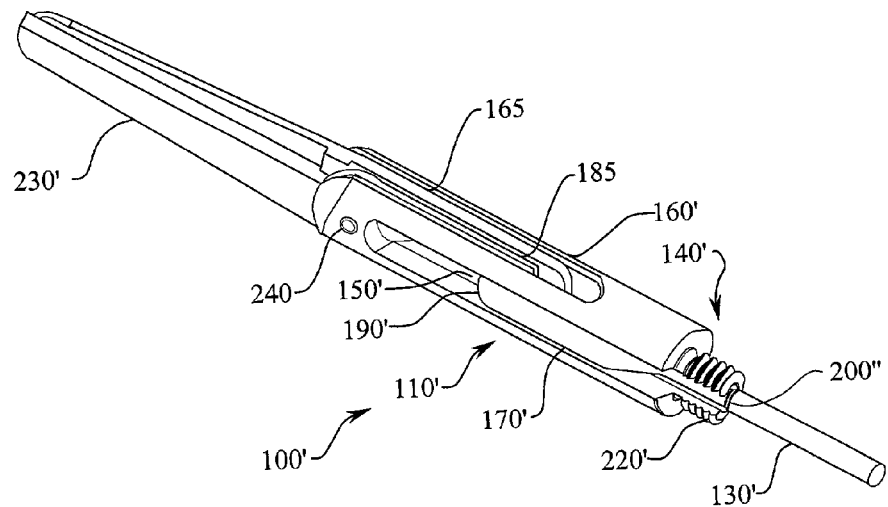
FIG. 5 is an elevated perspective view, in enlarged scale, of a modification of the reconfigurable surgical apparatus shown in FIG. 1, with some structure removed for clarity.

With reference now also to FIG. 5, any of the preceding embodiments may be further modified to incorporate a modified prime mover 130' that includes an anchor 170' adapted for compatibility with an interchangeable surgical tool 160' that receives the anchor 170' in an integrally formed capture member 150', which may or may not also include any other connecting structure. Further alterations to this variation may also incorporate a frangible portion 200" that may be formed in any element of the coupler 140', such as, for example, on the prime mover 130'. In FIG. 5, reference numerals with primes denote structural elements similar or identical to analogous components in the other figures that are identified by reference numerals without any prime or with double primes.

Figure 6:
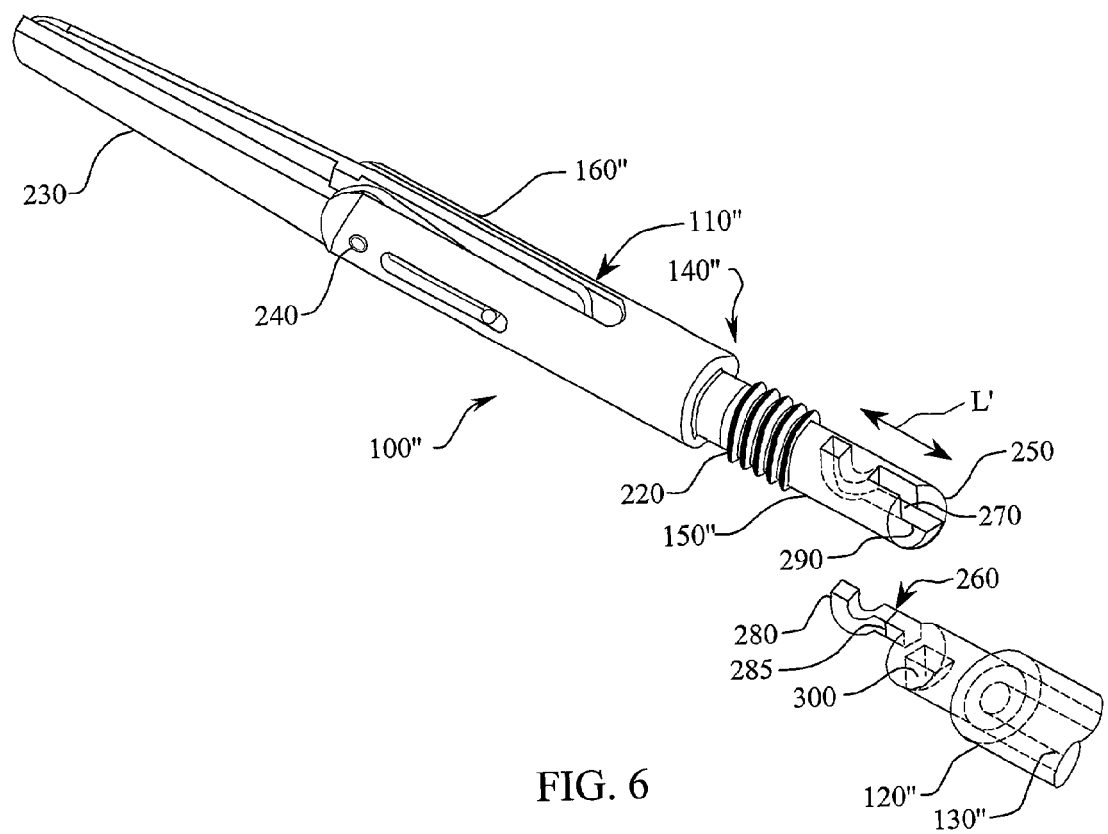
FIG. 6 is an elevated perspective view, in enlarged scale, of a variation of the reconfigurable surgical apparatus shown in FIG. 1.

The instant invention is also further directed to embodiments that include a reconfigurable surgical apparatus 100", such as that shown in FIG. 6, which includes many of the preceding features, elements, components, and capabilities. Here, as with preceding illustrations, similar reference numerals having primes or double-primes refer generally to similar or like components and elements depicted in drawings and figures described above. In FIG. 6, the apparatus 100" also further includes a coupler 140" that has a receiver 250 formed in an interchangeable surgical tool 160". The receiver 250 is adapted to releasably capture an engager 260 that is formed in a distal end of a hollow manipulation shaft 120" of the apparatus 100". The receiver 250 defines a recess 270 that is shaped to receive and capture an interlocking projection 280 that forms an outwardly projecting portion of the engager 260.

The exemplary configuration of the apparatus 100" shown in FIG. 6 may also further incorporate an engagement shelf 290 projecting from the receiver 250 and an alignment slot 300 adapted to receive and capture the engagement shelf 290. As with previous embodiments, the instant configuration may also further include a frangible portion 285 that may be formed in any of the components, and which is reflected in FIG. 6 as a scored region formed in the interlocking projection 280. Although a wide array of suitable profiles may be compatible for purposes of the instant invention, a generally hook shaped engager projection 280 is shown in FIG. 6, which is adapted to be received in the substantially hook shaped receiver 250 that is formed in the capture member 150" of the tool 160". Any of the previously described locking features and elements may be formed on the projection 280 and the receiver 250 to establish a "snap" together connection that can be forced apart only be severing the frangible portion 285.

INDUSTRIAL APPLICABILITY

The present invention provides the medical community with a surgical instrument that prevents the re-use of the operative portion through the incorporation of a frangible portion. This provides insurance that surgical procedures will be started with the sharpest and most sterile surgical instruments.

Numerous alterations, modifications, and variations of the preferred embodiments disclosed herein will be apparent to those skilled in the art and they are all anticipated and contemplated to be within the spirit and scope of the instant invention. For example, although specific embodiments have been described in detail, those with skill in the art will understand that the preceding embodiments and variations can be modified to incorporate various types of substitute and or additional or alternative materials, relative arrangement of elements, and dimensional configurations for compatibility with the myriad possible surgical interventions and endoscopic procedures. Accordingly, even though only few variations of the present invention are described herein, it is to be understood that the practice of such additional modifications and variations and the equivalents thereof, are within the spirit and scope of the invention as defined in the following claims.

We claim:

1. A reconfigurable surgical apparatus, comprising:
   a surgical instrument assembly formed with a hollow manipulation shaft internally receiving a prime mover activated by an actuator located at a proximal end of the shaft;
   a coupler formed about a distal end of the shaft and having a capture ledge;
   an interchangeable surgical tool attachable to the coupler and including an anchor adapted to cooperate with and mate to the capture ledge, such that a rotational force applied to the prime mover is transmitted between the prime mover and the tool;
   wherein said anchor is formed with at least one generally hook shaped tine, formed with a frangible portion, that includes an engagment face adapted to cooperate with and non-releasable engage the capture ledge; and
   wherein said anchor is formed with the frangible portion designed to break in an orientation substantially orthogonal to a direction of translation of the prime mover.

2. The apparatus according to claim 1, wherein the capture ledge is further formed in the coupler to define at least one lateral recess adapted to cooperate with and receive the anchor thereby transferring rotational force from the prime mover to the tool.

3. The apparatus according to claim 1, wherein the frangible portion is substantially sealed from an exterior environment by the coupler and the manipulation shaft.

4. A reconfigurable surgical apparatus, comprising:
   a surgical instrument assembly formed with a hollow manipulation shaft internally receiving a prime mover activated by an actuator located at a proximal end of the shaft;
   a coupler formed about a distal end of the shaft having a capture ledge that defines a recess in the coupler;
   an interchangeable surgical tool adapted to cooperate with and connect to the coupler comprising a frangible portion and an anchor adapted to cooperate with and non-releasably mate to the capture ledge thereby transferring a rotational force applied to the prime mover from the prime mover to the tool, the frangible portion being adapted for receipt in the recess after the anchor has been removed from the tool; and
   wherein said anchor is formed with the frangible portion designed to break in an orientation substantially orthogonal to a direction of translation of the prime mover.

5. A reconfigurable surgical apparatus, comprising:
   a surgical instrument assembly formed with a hollow manipulation shaft internally receiving a prime mover activated by an actuator located at a proximal end of the shaft;

a coupler formed about a distal end of the shaft and incorporating an anchor;

an interchangeable surgical tool adapted to cooperate with and connect to the coupler and formed with a capture ledge adapted to cooperate with and mate to the anchor thereby transferring a rotational force applied to the prime mover from the prime mover to the tool;

wherein said anchor is formed with at least one generally hook shaped tine, formed with a frangible portion, that includes an engagement face adapted to cooperate with and non-releasable engage the capture ledge; and wherein said anchor is designed to break in an orientation substantially orthogonal to a direction of translation of the prime mover.

6. The apparatus according to claim 5, wherein the capture ledge is further formed in the tool to define at least one lateral recess adapted to cooperate with and non-releasably receive the anchor.

7. A reconfigurable surgical apparatus, comprising:

a surgical instrument assembly formed with a hollow manipulation shaft internally receiving a prime mover activated by an actuator located at a proximal end of the shaft;

a coupler formed about a distal end of the shaft to have a generally hook shaped anchor having an engagement face;

an interchangeable surgical tool formed at an end with a capture ledge that defines a lateral recess in the tool, the ledge being adapted to cooperate with and mate to the engagement face thereby transferring a rotational force applied to the prime mover from the prime mover to the tool;

wherein said anchor is formed with a frangible portion, that includes an engagement face adapted to cooperate with and non-releasably engage the capture ledge; and wherein said anchor is designed of break in an orientation substantially orthogonal to a direction of translation of the prime mover.

8. A reconfigurable surgical apparatus, comprising:

a surgical instrument assembly formed with a hollow manipulation shaft internally receiving a prime mover activated by an actuator located at a proximal end of the shaft;

a coupler formed about a distal end of the shaft and formed with an anchor;

an interchangeable surgical tool configured to connect to the coupler and formed with a reciprocating capture member adapted to cooperate with and non-releasably mate to the anchor thereby transferring a rotational force applied to the prime mover from the prime mover to the tool;

wherein said anchor is formed with at least one generally hook shaped tine, formed with a frangible portion; and wherein said anchor is formed with the frangible portion designed to break in an orientation substantially orthogonal a direction of translation of the prime mover.

9. The apparatus according to claim 8, wherein the capture member is further formed in the tool to define at least one lateral recess adapted to cooperate with and receive the anchor.

10. A means for performing an intracorporeal surgical procedure, comprising:

a means for imparting a range of motion;

a means for defining an intracorporeal passageway connected at a proximal end to the motion imparting means, the passageway being internally received with a means for transmitting the imparted range of motion;

a means for distally coupling the passageway means that defines a means for anchoring;

an interchangeable means for performing a surgical intervention that includes a means for capturing the anchoring means;

wherein the interchangeable intervention means is, when mated to the anchoring means, remotely actuatable by operation of the motion imparting means and thereby transmits a rotational force applied to the motion imparting means between the motion imparting means and the interchangeable intervention means;

wherein said anchoring means is formed with at least one generally hook shaped tine that includes an engagement face adapted to cooperate with and non-releasably engage the means for capturing; and wherein the means for anchoring is further formed with a means for defining a frangible portion of the anchoring means designed to break in an orientation substantially orthogonal to a direction of translation of the motion imparting means.

11. The means for performing an intracorporeal surgical procedure according to claim 10, wherein the capturing means is further formed in the intervention means to define at least one means for defining a lateral recess adapted to cooperate with and non-releasably receive the anchoring means.

12. The means for performing an intracorporeal surgical procedure according to claim 11, wherein the anchoring means is formed as a generally hook shaped tine having an end sized for non-releasable receipt into the recess.

13. The means for performing an intracorporeal surgical procedure according to claim 11, wherein the anchoring means is formed with a frangible portion defining means adapted to cooperate with and be removably received in the recess after the frangible portion defining means has been severed.

* * * * *